(12) United States Patent
Ware (10) Patent No.: US 9,468,799 B1
(45) Date of Patent: Oct. 18, 2016

(54) ORTHOPEDIC SUPPORT AND EXERCISE DEVICE

(71) Applicant: PIPECONTROL LLC, Madison, MS (US)

(72) Inventor: Arthur Nelson Ware, Madison, MS (US)

(73) Assignee: PIPECONTROL LLC, Madison, MS (US)

( * ) Notice: Subject to any disclaimer, the term of this patent is extended or adjusted under 35 U.S.C. 154(b) by 0 days.

(21) Appl. No.: 14/700,317

(22) Filed: Apr. 30, 2015

(51) Int. Cl.
| | |
|---|---|
| A63B 21/06 | (2006.01) |
| A63B 22/20 | (2006.01) |
| A61F 5/01 | (2006.01) |
| A61F 5/058 | (2006.01) |
| A63B 21/00 | (2006.01) |
| A63B 23/04 | (2006.01) |

(52) U.S. Cl.
CPC .............. *A63B 22/20* (2013.01); *A61F 5/0111* (2013.01); *A61F 5/0585* (2013.01); *A63B 21/0004* (2013.01); *A63B 21/06* (2013.01); *A63B 21/4043* (2015.10); *A63B 23/04* (2013.01)

(58) Field of Classification Search
CPC .. A63B 22/20; A63B 21/06; A63B 21/4043; A63B 21/0004; A63B 23/04; A63B 21/4011; A63B 21/4013; A63B 21/4015; A63B 21/4037; A63B 21/4039; A63B 22/201; A63B 23/03508; A63B 23/0482; A63B 23/0488; A63B 23/0494; A63B 23/08; A63B 23/085; A63B 23/10; A61G 2005/127; A61G 7/0075; A61G 13/1245; A47C 20/201

USPC .............................................. 128/45, 46, 882
See application file for complete search history.

(56) References Cited

U.S. PATENT DOCUMENTS

| | | | | | |
|---|---|---|---|---|---|
| 4,229,001 | A | * | 10/1980 | Roman | A63B 21/012 482/114 |
| 4,779,296 | A | * | 10/1988 | Bond | A47C 20/021 5/646 |
| 4,896,879 | A | * | 1/1990 | Klawitter | A63B 21/0602 482/105 |
| 5,978,991 | A | * | 11/1999 | Miles | A47C 20/021 5/504.1 |
| 9,108,080 | B2 | * | 8/2015 | Cataldi | A61H 1/0259 |
| 2002/0128134 | A1 | * | 9/2002 | Huang | A63B 22/20 482/148 |

* cited by examiner

*Primary Examiner* — Loan H Thanh
*Assistant Examiner* — Megan Anderson
(74) *Attorney, Agent, or Firm* — Workman Nydegger (57) ABSTRACT

An orthopedic support and exercise device may be used to help patients regain strength and mobility during lower limb rehabilitative exercises. An orthopedic support and exercise device may include a foot support body; a rotation restraint wall extending vertically upward on one side of the foot support; a divider wall extending vertically upward from the support body and extending transversely from an opposing side of the foot support body; an ankle bed rest defined by a space between the rotation restraint wall and the divider wall such that a foot placed on the orthopedic support and exercise device with ankle in the ankle bed rest is prevented from rotational movements during extension and flexion of a leg; and a weighted slider with a smooth bottom surface that is attached at a base of the foot support body.

19 Claims, 9 Drawing Sheets

ORTHOPEDIC SUPPORT AND EXERCISE DEVICE

BACKGROUND

Patients often require rehabilitative exercises to strengthen and restore movement of their limbs following injury or surgery. Exercises may include movements that focus on certain muscles in need of strengthening or restoration of movement. Patients may be unable to perform certain movements, however, without supporting the target limb or supporting other limbs. For example, neurological patients and orthopedic patients may require lower extremity support for rehabilitation of knee, ankle, and hip joint movement exercises.

Additionally, support devices may be needed to isolate movements among one or more defined joint movements, such that the movement exercise is limited to one or few joint movements.

Thus, improved support devices are needed to both isolate and facilitate proper movements for rehabilitative purposes. Moreover, improved support devices are needed for other environments, such as training purposes and exercise regimes.

BRIEF SUMMARY

The following generally relates to support apparatus and methods for ensuring proper limb support and isolated joint movement. The orthopedic support and exercise device may be used to help patients in a rehabilitative environment or other environment, such as for training or regular exercise. The patient, or user, may lie in positions that include supine position and side position, as well as prone position, to allow for various sliding movements of the lower limb with the ankle joint supported and at least partially limited from certain movements throughout the sliding movement exercise.

The orthopedic support and exercise device may comprise a foot support body that includes a plurality of walls for providing support and restraint. For example, a rotation restraint wall and divider wall may be used to prevent rotational movements such as hip rotation and knee flexion. Support and isolation for the ankle joint may be found in an ankle bed rest, the ankle bed rest defined by a space between the rotation restraint wall and the divider wall such that a foot placed on the support and exercise device with ankle in the ankle bed rest is prevented from rotational movements.

Sliding exercise movements may further be facilitated with a weighted slider with a smooth bottom surface that is attached at a base of the foot support body. Other features and advantages may be readily ascertained.

DETAILED DESCRIPTION

The following generally relates to ensuring proper limb support and isolated joint rotational movement using an orthopedic support and exercise device. The orthopedic support and exercise device may be used to help patients in a rehabilitative environment or other environment, such as for training or regular exercise. The patient, or user, may lie in positions that include supine position and side position (as well as prone) to allow for various sliding movements of the lower limb with the ankle joint supported throughout the sliding movement exercise.

The orthopedic support and exercise device may comprise a foot support body that includes several walls for providing support and restraint. For example, a rotation restraint wall and divider wall may be used to prevent rotational movements such as hip rotation and knee flexion. Support and isolation for the ankle joint may be found in an ankle bed rest, the ankle bed rest defined by a space between the rotation restraint wall and the divider wall such that a foot placed on the orthopedic support and exercise device with ankle in the ankle bed rest is prevented from rotational movements.

Sliding exercise movements may further be facilitated with a weighted slider with a smooth bottom surface that is attached at a base of the foot support body. Other features and advantages may be readily ascertained.

Figure 1A:
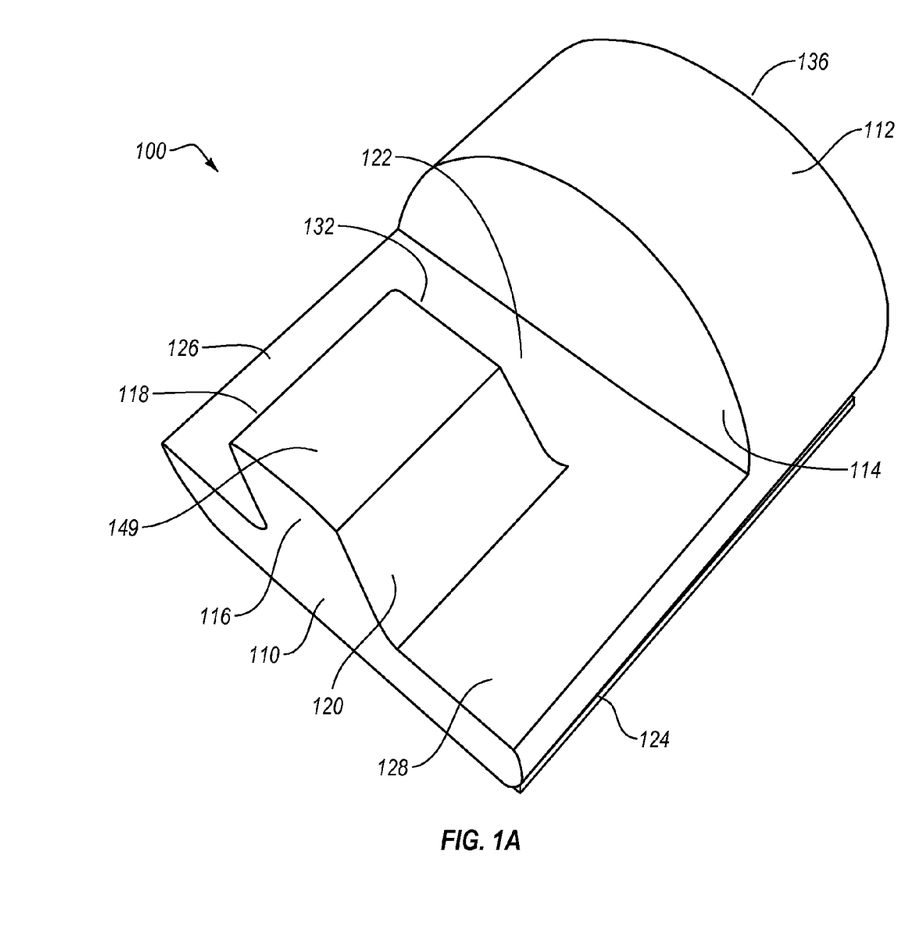
FIG. 1A depicts a perspective view of an orthopedic support and exercise device.

Turning to FIG. 1A, a perspective view of an orthopedic support and exercise device 100 is shown, comprising foot support body 110, rotation restraint wall 112, inner side 114 of rotation restraint wall 112, divider wall 116, inner right foot surface 118, inner left foot surface 120, ankle bed rest 122, weighted slider 124, top platform 126, bottom platform 128, top surface 136 of rotation restraint wall 114, top surface 149 of divider wall 116, and divider inner side 132.

The foot support body 110 may be a generally flat main body, including a block shape with curved or rounded sides and corners as shown. Embodiments include the shape as being oblong, circular, or other shapes as desired. The foot support body length may be longer than the cross-wise width or the cross-wise width may be longer than the length. Edges may be defined with sharp or curved edges, or a combination thereof.

From the foot support body 110, the rotation restraint wall 112 extends vertically upward and is located near or at along one side of the foot support body 110. The rotation restraint wall 112 may span a desired length along the width of the foot support body 110, or span the entire side of the foot support body 110. Embodiments include that the rotation restraint wall 112 have a length that extends beyond one or more foot support body edges, creating an overhang wall formation.

The width, or wall thickness, of the rotation restraint wall 112 may vary. As shown, the width may start at a side edge of the foot support body 110 and end before a centerline or a center area of the foot support body 110. Embodiments include that the width not reach to the outer side edge of the foot support body 110. Also, embodiments include widths that reach the center area of the foot support body 110 or past the center area. Although the width of the rotation restraint wall 112 is shown as being homogeneous with the inner side 114 extending crosswise from opposite ends in a perpendicular manner, the width may have varying dimensions such that the inner side 114 extends in a path that is not truly crosswise. For example, near or at the center area where the ankle is located, the inner side 114 may have a hollowed out indention or space section. Thus, the width of the inner side 114 may be narrowed or tapered inward near or at the region where the ankle is located. The inner side 114 may have a notch or cavity removed to form the indention. Alternatively, an entire sectional portion of the restraint wall may form the indention, forming a curved wall that tapers inward to form a hollowed section. Because the orthopedic support and exercise devices may be used for both feet, there may be two hollowed sections, one for each foot. Also, there may be one long hollowed section to accommodate each foot.

As shown, the top surface 136 of the rotation restraint wall 112 may be curved, with a flat, smooth surface that curves around in an upside down cupping shape. Any suitable number of tops may be provided, however. For example, instead of a curved shape, the top 149 may be completely flat, creating a standard wall appearance. Alternatively, one or more visually appealing curvatures and shapes may be incorporated to the top surface 136 to increase the appearance or functionality, and thus heighten user experience. The top 149 of divider wall 116 may have similar types of variation in height, thickness, curvatures, and shapes.

Inner side 114 of rotation restraint wall 112 is used to provide a surface which can be used by a heel of the foot when, for example, a user is lying down in a side position, and pushing against the inner side 114 to make leg movements, such as hip extension and knee flexion. When lying down in a side position with the foot in a side position, the foot rests on a top platform 126 or bottom platform 128, depending on which foot is using the orthopedic support and exercise device 100. The portion of the right foot below the right ankle rests on the top platform 126, or in other words, the surface area of the foot support body 110 that is above the divider wall 116. The portion of the left foot below the left ankle rests on the bottom platform 128, or in other words, the surface area of the foot support body 110 that is below the divider wall.

Adjacent to the top platform 126 is the inner right foot surface 118, or the surface of the divider wall intersecting with the top platform 126, which may be pushed against by right foot. Adjacent to the bottom platform 128 is the inner left foot surface 120, or the surface of the divider wall intersecting with the bottom platform 128, which may be pushed against by the left foot.

When the left foot is being used with the orthopedic support and exercise device 100, the orthopedic support and exercise device 100 is flipped around, or rotated 180 degrees, such that the bottom platform 128 area is positioned where the top platform 126 is for the right foot. When flipped around, the rotation restraint wall 112 is positioned on the opposite side as where it is positioned for the right foot.

When lying down in a supine position with toes pointed generally upward, outer side of the heel may be used to push against the inner side 114 of the rotation restraint wall 112 to make leg movements, such as hip abduction. Additional movements may be possible by pushing against the rotation restraint wall 112.

Also supporting movement and preventing rotational movement is inner side 132 of divider wall 116. As shown, divider wall 116 extends vertically upward from the foot support body 110, similar to the rotation restraint wall 112. The divider wall 116 extends transversely, or crosswise, along the foot support body 110, from a side opposite and across from the rotation restraint wall 112, to a location at or near a mid-section of the foot support body 110. The manner in which the divider wall 116 extends may be parallel to a lengthwise axis of the foot support body 110. In other words, the divider wall 116 may extend perpendicularly from the midpoint of the side. Alternatively, the divider wall 116 may extend from a point other than the midpoint of the side. The divider wall 116 may extend past the side of the support body to create an overhang. The width, or thickness, of the divider wall 116 may be similar in proportion to a width of all or a portion of a standard ankle or heel portion. The width of the divider wall 11 may be similar to or the same as the width of the rotation restraint wall 112. The width may be dimensioned more or less as desired. The width may vary along the length of the divider wall to provide a desired point of contact with the foot. Other variations are anticipated.

One or both of the rotation restraint wall 112 and the divider wall 116 may extend generally vertically upward to a height of at least a general foot length according to anatomical measurements of a standard person. A standard person is a mathematical model of a person based on any suitable data that simulates a person's size, body proportions, and the like. The model can be based upon data, for example, used in the clothing and shoe industry to define sizes for apparel and the like. The standard person used and the data set used to derive the standard person is chosen with the user of the orthopedic support and exercise device 100 in mind and can be based upon average values of body proportions from any sample of the population from, for example, total population, gender, age, body size or weight, nationality, or the like. The standard person may also be based upon any particular individual, or group of individuals. Thus, the standard person for a particular orthopedic support and exercise device 100 may be designed for marketing to the public in general or be customized to fit a particular group of people, or to fit an individual.

Accordingly, the heights of the rotation restraint wall 112 and the divider wall 116 may be the same or different. Embodiments include that the height be increased and decreased using panels or removable wall elements. Standard adhesives, clips, screws, straps, or other means may be used for securement of the panels or removable wall elements.

An ankle bed rest is shown with a surface defined by a space between the inner side 114 of the rotation restraint wall 112 and the inner side 132 of the divider wall 116 such that a foot placed on the orthopedic support and exercise device 100 with the ankle in the ankle bed rest is prevented from certain rotational movements during movements associated with extension and flexion of a leg and/or knee.

The ankle bed rest may be spaced to provide a tight fit or relaxed fit. Furthermore, the ankle bed rest may be spaced with ample wiggle room to the extent that that the ankle need not even touch the inner sides 114 and 132, at least when at rest.

Embodiments include that the ankle bed rest have adjustments such that the space may be increased or decreased, as needed. For example, the divider wall 116 may be lengthened or shortened as needed or desired. The divider wall 116 may move inward and outward along the foot support body 110 to form a smaller or larger space, respectively. Alternatively, inserts may be added and removed to either or both the inner side 132 of the divider wall 116 and the inner side 114 of the rotation restraint wall 112 to change the size of the ankle bed rest space. Appropriate attachments for adjustments may include screws, clamps, straps, and other means commonly known in the art.

Also, materials may be added to provide further support, compression, structure, and weight. For example, cushioning may be added along the inner side 114 of the rotation restraint wall 112 or inner side 132 of the divider wall 116 to provide a snug or tight fit when a foot is inserted. Cushioning may be added along the inner side 114 of the rotation restraint wall 112 or the inner side 132 of the divider wall 116 in specific areas, for example, near or at the location where the ankle is anticipated to be placed. Alternatively, cushioning may be added on only one side, the inner side 114 of the rotation restraint wall 112 or the inner side 132 of the divider wall 116 at or near the location where the ankle is anticipated to be placed. Cushioning may be added with cutaways or surface definitions in the shape of a standard foot corresponding to various positions anticipated for the foot.

For structural stability and support, weighted elements may be added within the interior or on the exterior of the rotation restraint wall 112, the divider wall 116, ankle bed rest, or other areas of the orthopedic support and exercise device 100. For example, the rotation restraint wall 112 may further comprise a stiff layer, such as an aluminum surface layer or siding, located along the inner side 114 to protect and provide structural support for the rotation restraint wall 112. Other support elements may be readily ascertained.

The rotation restraint wall 112, along with the divider wall 116, prevents rotational movement of the hip. The following movements may be limited or prevented entirely:

Dorsiflexion: Bending the foot at the ankle toward the shin (bending the foot upward).
Plantar flexion: Bending the foot at the ankle toward the sole (bending the foot downward).
Eversion: Turning the foot so the sole faces laterally.
Inversion: Turning the foot so the sole faces medially.
Circumduction: Moving a part so that its end follows a circular path (moving the toes in a circular motion without significantly moving the ankle).

Other movements may be limited or prevented also. In addition to preventing movements of the foot, the orthopedic support and exercise device prevents rotational movements of the leg. Internal and external rotation of the knee or leg may be prevented. For example, the knee may be prevented from turning inwardly or outwardly to face a direction other than a direction that is parallel to the direction of the foot. The foot naturally tends to turn away from the body when lying in a supine position and such rotation of the foot provides torque or torsional effects on the leg. The rotation restraint wall 112, however, prevents this from happening.

In preventing rotation, a leg may be forced to stay in a generally fixed position such that ice may be applied to a region of the leg to reduce swelling or ease pain (and gain extension motion at the knee). In providing support, orthopedic and neurological patients with reduced strength or limited mobility may be able to accomplish the rehabilitative therapy needed to regain strength, lasting mobility, and even recovery of full range of motion. Along with providing support, the ankle bed rest 122 is advantageous because it makes the orthopedic support and exercise device 100 easy to put on and take off.

At a base or bottom of the foot support body 110 is a weighted slider 124. The slider 124 may comprise a body that is weighted and has a smooth bottom surface attached to the base of the foot support body 110. The smooth bottom surface may be slick to allow the device to slide or glide with relative ease along most, if not all surfaces, including uneven terrain, carpet, laminate, wood flooring, and other types of flooring. The weighted slider 124 may be attached in a flush manner with the base of the foot support body 110 such that the entire surface of the weighted slider rests flat against the base of the foot support body 110. The weighted slider 124 may comprise wood, plastic, metal, composite, laminate, or other material. The slider may be polished, such as polished wood, or polished laminate.

Weighting of the slider is useful because it provides support as well as a stable platform on the bottom of the foot support body 110. It is also useful in movements associated with the orthopedic support and exercise device 100, such as gliding in back and forth movements. Because the foot support body 110 may not be rigid, the slider may provide added rigidity and stability that strengthens the orthopedic support and exercise device 100.

Figure 1B:
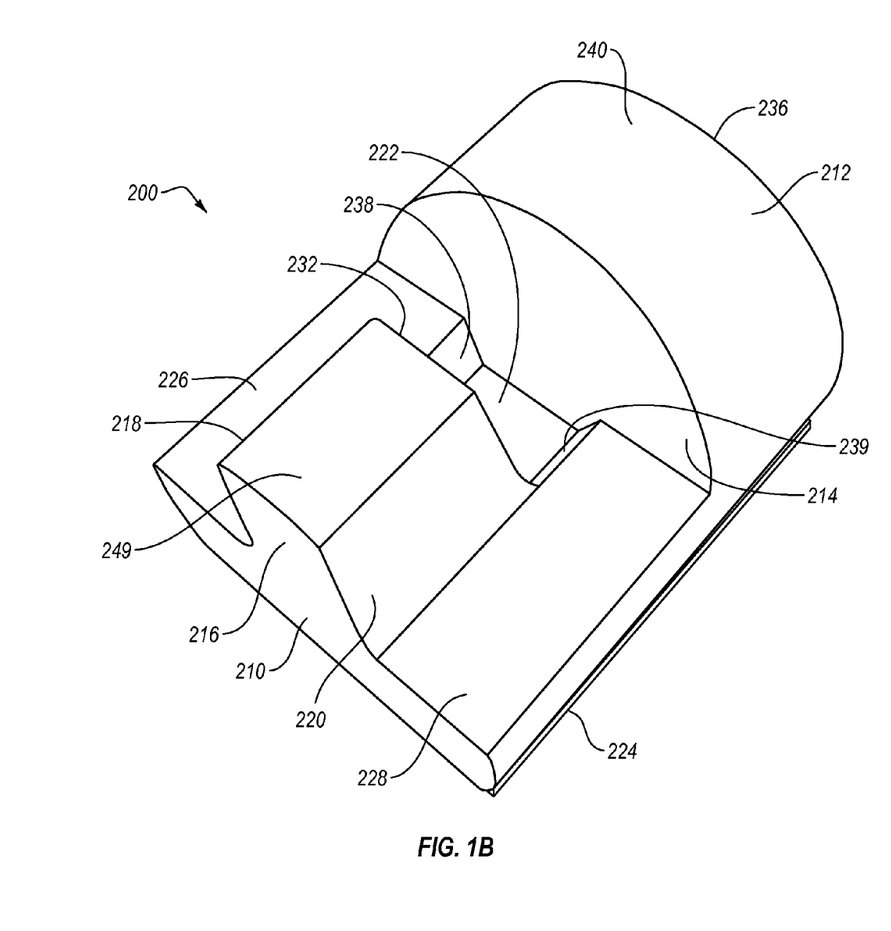
FIG. 1B depicts a perspective view of an orthopedic support and exercise device with notch.

Turning to FIG. 1*b*, an orthopedic support and exercise device 200 is shown, including foot support body 210, rotation restraint wall 212, inner side 214 of rotation restraint wall 214, divider wall 216, inner right foot surface 218, inner left foot surface 220, weighted slider 224, top platform 226, bottom platform 228, divider inner side 232, top surface 236 of rotation restraint wall 212, top surface 249 of divider wall 216, angled sidewalls 238 and 239, notched ankle bed rest 222, angled sidewalls 238 and 239, and skin layer 240.

As in FIG. 1A, the orthopedic support and exercise device 200 of FIG. 1*b* includes a rotation restraint wall 212 to provide support and stability for the ankle during sliding movement exercises. Also, the orthopedic support and exercise device 200 prevents rotation, such as internal rotation and external rotation, of the knee. The ankle is also prevented from joint rotations.

For sliding movements, the rotation restraint wall 212 and the divider wall 216 restrain movement of the foot. With the right foot resting on the top platform 226, the inner right foot surface 218 of the divider wall 216 may be pressed against by a top front area of the right foot. With the left foot resting on the bottom platform 228, the inner left foot surface of the divider wall 216 may be pressed against by a top front area of the left foot.

An ankle may be placed between the divider inner side 232 and the inner side 214 of the rotation restraint wall 212 and the foot may press against the inner sides 214 and 232 during sliding movements, whether the user is in a side position, supine position or other position.

The top surface 236 of the rotation restraint wall 214 and the top surface 249 of the divider wall 216 may have variations in height, variations in design, as well as variations in location, as desired. Heights may correspond to standard feet length or slightly longer, such as 1 to 2 inches longer than standard feet length. The heights may be the same or different. One of the walls 212 and 216 may be weighted or have materials added to increase durability and strength in the wall.

For the ankle, embodiments may include the notched ankle bed rest 222, which includes a notch, divot, recess, or carved cutout area that is anatomically dimensioned with lengths and widths, circumference, edging, or other dimensioning, that conform to a standard heel and standard ankle member. The area may be larger or somewhat smaller than a heel and ankle member. The recess may be a general ankle width or heel width in depth, corresponding to standard anatomical measurements. The recess may extend horizontally between the divider wall 216 and the rotation restraint wall 212. Also, the recess may extend vertically at least a length equal to a width of the divider wall 216. The recess may further extend to a length greater than the width of the divider wall 216. The recess may span up to the entire width of the foot support body 210.

This recessed area may provide a meaningful grip for the heel or ankle to use and to apply pressure when pushing and pulling, extending and retracting, and performing movements provided herein. The ankle and heel may rest comfortably within the recess of the ankle bed rest 222, with placement that conforms to and supports the user's foot and ankle in use.

Note that the ankle bed rest 222 may have angled sidewalls 238 and 239 on opposing sides, as shown. The sidewalls 238 and 239 may have curvature, such as a seamless curvature from horizontal to vertical positions, such that there are no sharp edges. Alternatives include that the sidewalls 238 and 239 extend generally vertical upward, like the rotation restraint wall 212 and the divider wall 216. Edges may be curved or have other surfacing features. Edges, as well as other surfaces described herein, may be smooth, pebbled, rough-textured, contoured, or have other features that improve and aid the user experience. For example, a textured surface may improve foot grip with the orthopedic support and exercise device.

Embodiments further include that the ankle bed rest 222 have cushioning to provide comfort. Extra material or padding may be added to provide a snug fit for the ankle and further prevent joint rotational movements.

Embodiments further include that the foot support body has a height and/or flexibility, coupled with sufficient firmness, so as to maintain a minimum elevation of the patient's ankle of one inch up to one foot, from the surface beneath the orthopedic support and exercise device, whether it be a ground surface, level plane, or uneven terrain, during use. Also, embodiments include that the foot support body has a firmness with sufficient yield to reduce pressure at and provide a comfortable support for high-pressure, soft-tissue areas. Other parts of the slider support body may share these characteristics.

An orthopedic support and exercise device 200 may have a skin layer 240. The skin layer 240 may comprise a coating or extra surface layer on the exterior surface of the orthopedic support and exercise device 200. The skin layer 240 may cover the weighted slider 224 separately, however, embodiments include that the skin layer 240 be a covering that uniformly surrounds the entire orthopedic support and exercise device 200. Embodiments further include that the skin layer 240 cover one or more of the foot support body 210, the rotation restraint wall 212, the divider wall 216, and the weighted slider 224 separately.

The skin layer 240 may comprise a polymer coating or other coating. Note that the skin layer 240 may make the orthopedic support and exercise device 200 impermeable, fluid-impermeable, stain-resistant, radiolucent, or have other features that enable the orthopedic support and exercise device 200 to be reusable.

Figure 2A:
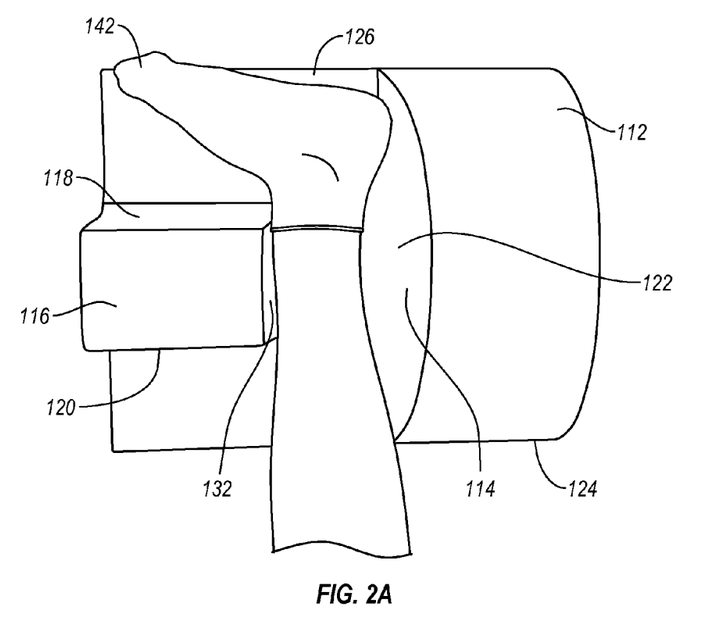
FIG. 2A depicts a top view of right foot inserted into the orthopedic support and exercise device and facing to a side.
Figure 2B:
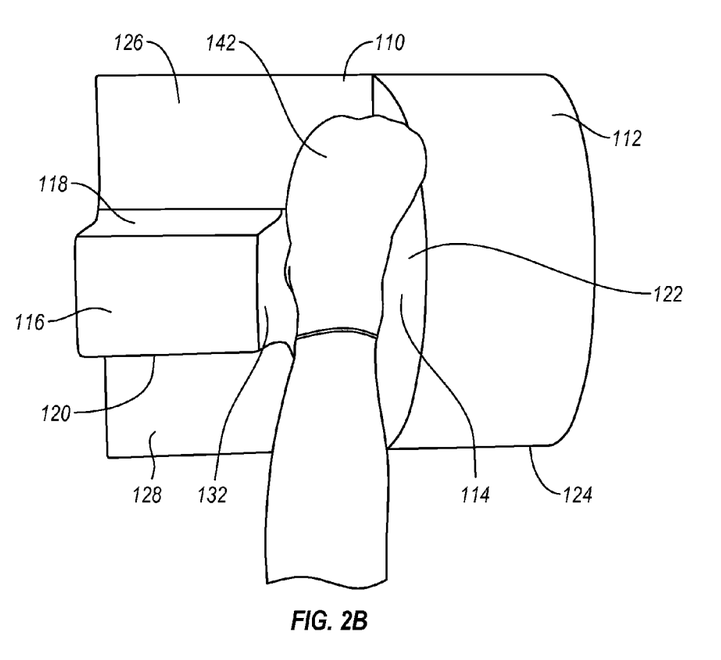
FIG. 2B depicts a top view of a right foot inserted into the orthopedic support and exercise device and pointing generally upward.
Figure 3A:
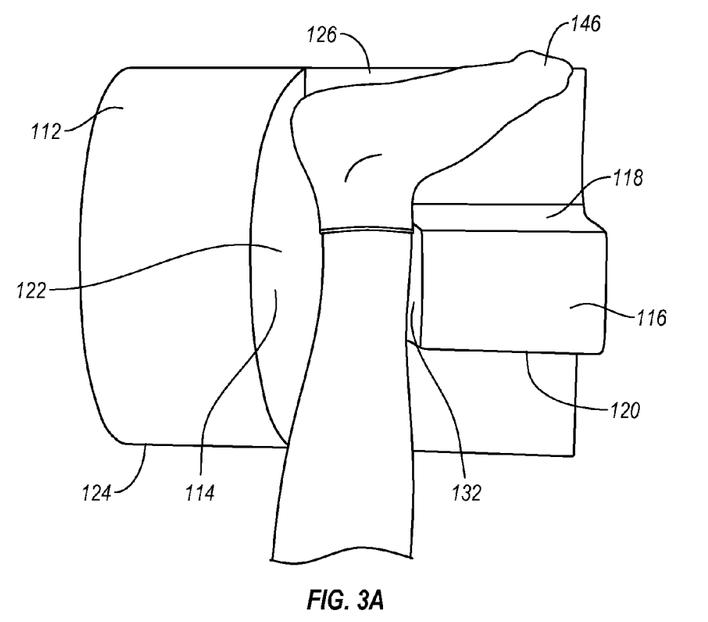
FIG. 3A depicts a top view of left foot inserted into the orthopedic support and exercise device and facing to a side.
Figure 3B:
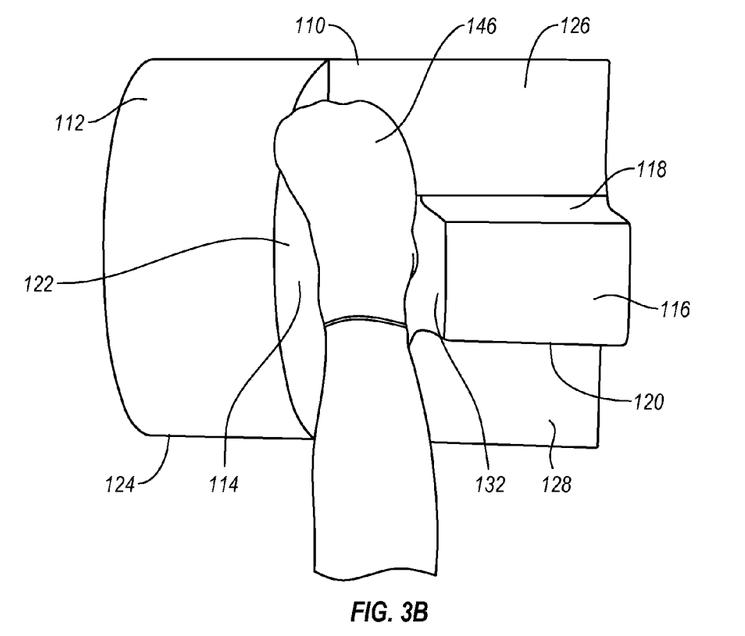
FIG. 3B depicts a top view of a left foot inserted into the orthopedic support and exercise device and pointing generally upward.

In FIGS. 2A and 2B, a right foot 142 is shown inserted into the orthopedic support and exercise device 100. In FIGS. 3A and 3B, a left foot 146 is shown inserted into the orthopedic support and exercise device 100. The divider wall 116 separates a top platform 126 and inner right foot surface 118 for right foot support and a bottom platform 128 and inner left foot surface 120 for left foot support. The top platform 126 and bottom platform 128 may be generally equal in dimension, however the surface areas may differ. The area provided may allow for a foot or a distal region of the foot to be supported before, during, and after movement. Because of the divider wall 116 and the rotation restraint wall 112, the foot is prevented from making movements such as dorsiflexion, plantarflexion, and other movements discussed herein.

For the ankle bed rest 122, the location of the inner side 114 of rotation restraint wall 112 and inner side 132 of divider wall 116 may vary, depending on the desired placement of the ankle relative to the foot support body 110. With the inner side 114 of the rotation restraint wall and inner side of divider wall 116 defining a central area relative to the foot support body 110, the ankle bed rest may be centered on the foot support body 110. Embodiments include placement of the ankle bed rest directly above the center of mass of the foot support body 110, which may not be a center relative to the plan view area of the foot support body 110. Embodiments include that the ankle bed rest 122 be located off center to the left or off center to the right of the foot support body 110. Further embodiments include that the ankle bed rest 122 be located above center or below center relative to the area of the foot support body 110. Thus, the ankle of right foot 142 may be properly isolated with restricted movement whether the user is lying in a supine position with toes facing generally upward or whether the user is lying on a side with toes facing toward a side.

In FIGS. 3A and 3B, a left foot 146 is shown inserted into the orthopedic support and exercise device 100 with FIG. 3A showing a side position and FIG. 3B showing a supine position. Because both left and right feet can be used with the device, the orthopedic support and exercise device 100 may help people with injuries, disabilities, weakness, or impaired mobility that occurs on either or both lower extremities. The user does not require a separate device for each foot. The user simply performs exercises on one foot, flips the device around, and performs exercises on the other foot.

Figure 4:
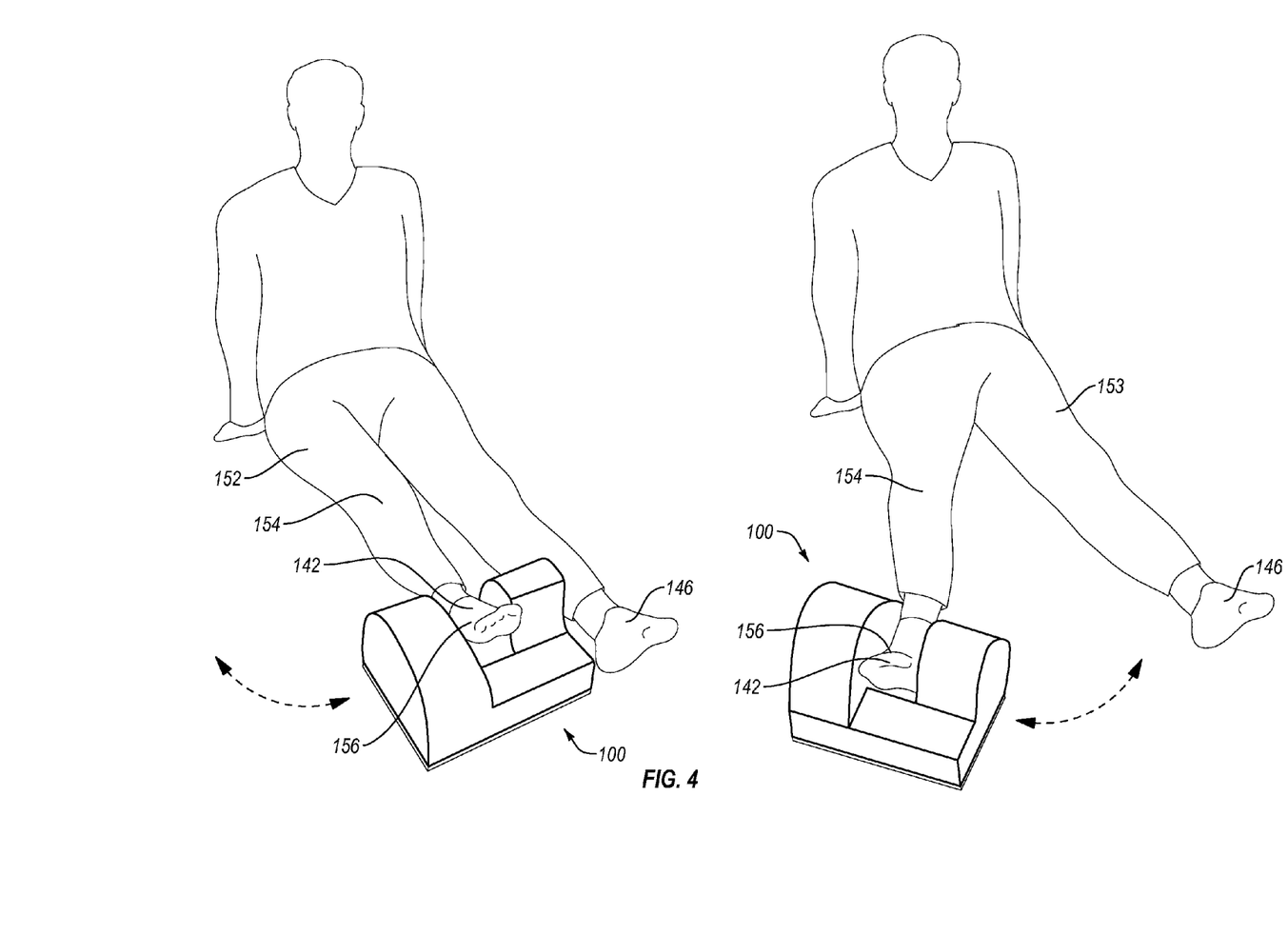
FIG. 4 depicts a user using the orthopedic support and exercise device for hip abduction, adduction.

Turning to FIGS. 4-7, exercise movements that may be performed with the orthopedic support and exercise device 100 are shown. In FIG. 4, a user is lying in a supine position and performs hip abduction and adduction movements with a lower limb inserted in the orthopedic support and exercise device 100 while the other limb remains in a neutral position. Here, the right leg 152 moves while the left leg 153 stays in a neutral position. With the orthopedic support and exercise device 100 rotated 180 degrees, the left foot 146 may make the abduction and adduction movements while the right foot 152 remains in a neutral position. Using the orthopedic support and exercise device 100, the right knee 154 may be prevented from external and internal rotation. Furthermore, the right ankle 156 may be prevented from various rotational movements described herein. Note that the knee and ankle rotation movements may be isolated in all of the movements described herein.

Figure 5:
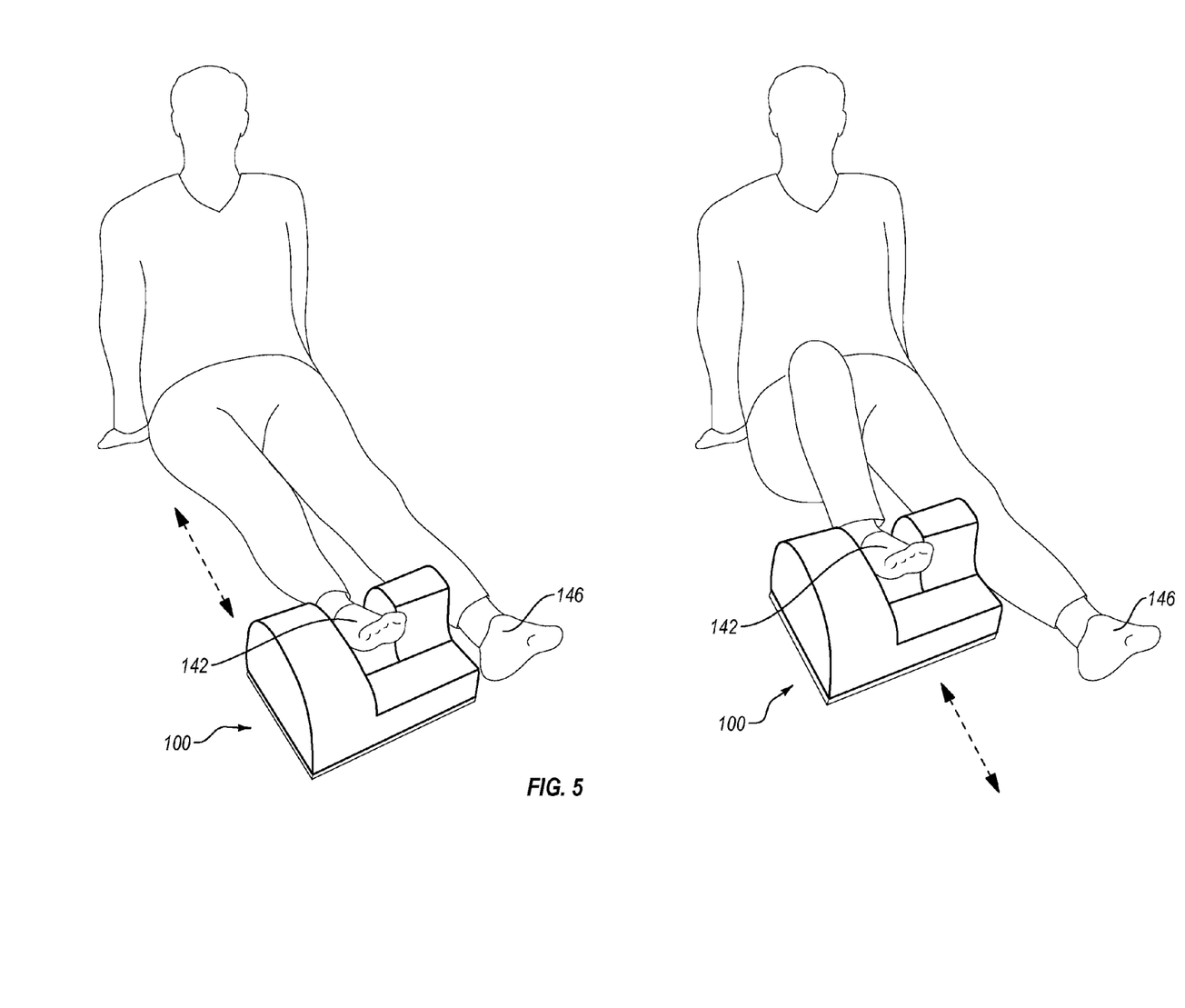
FIG. 5 depicts a user using the orthopedic support and exercise device for hip and knee flexion, extension.

In FIG. 5, a user lies in a seated or otherwise reclined position and performs combined knee plus hip flexion and extension movements with one lower limb in the device while the other limb remains in a neutral position. Here, the right foot 142 performs knee plus hip flexion and extension while the left foot 146 remains neutral. With the orthopedic support and exercise device 100 rotated 180 degrees, the left leg may perform hip flexion and extension while the right leg remains neutral.

Figure 6:
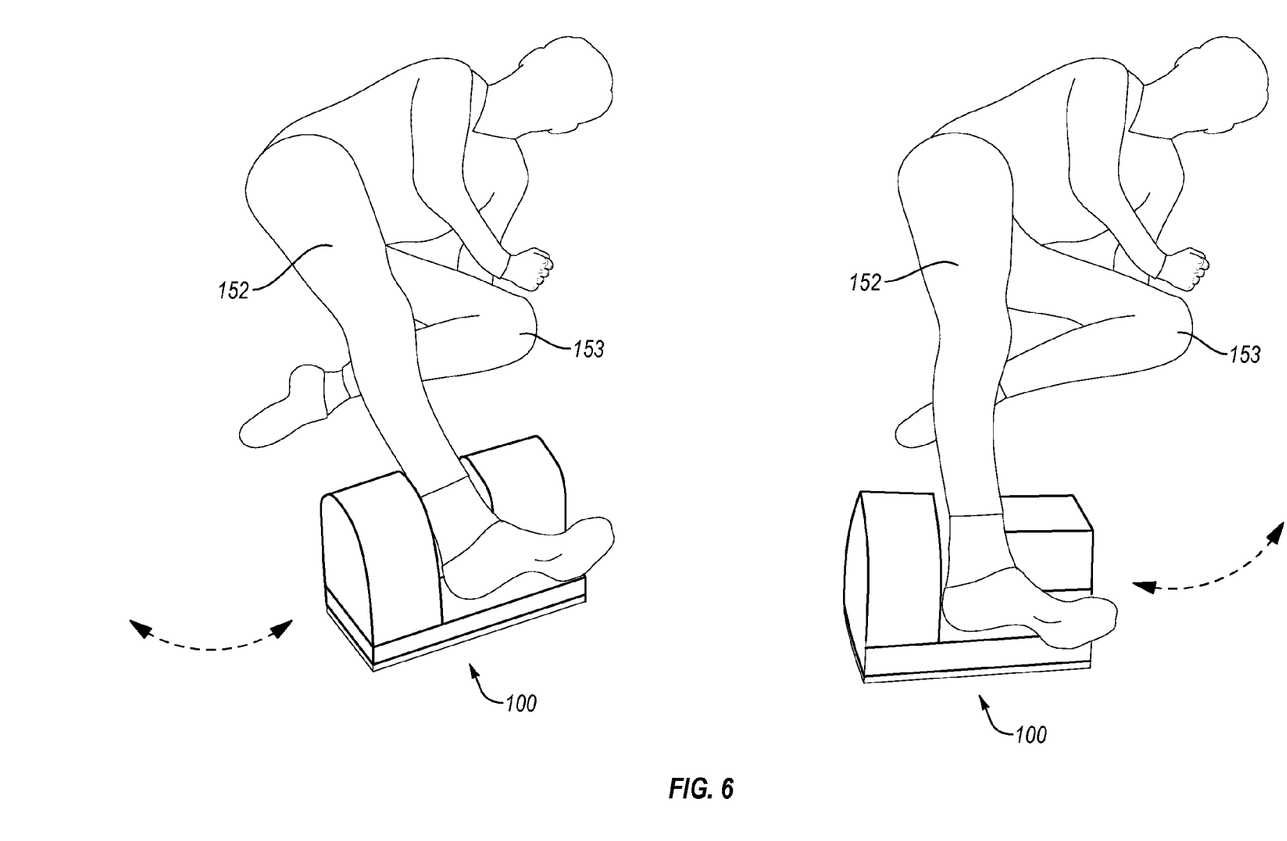
FIG. 6 depicts a user using the orthopedic support and exercise device for hip flexion, extension.

In FIG. 6, a user lies on a side and performs hip flexion and extension movements with one lower limb and the device while the other limb remains in a neutral position. Here, the right leg 152 performs hip flexion and extension while the left leg 153 remains neutral. Turning slider the support device 100 around 180 degrees, the left leg 153 may perform hip flexion and extension while the right leg 152 remains neutral.

Figure 7:
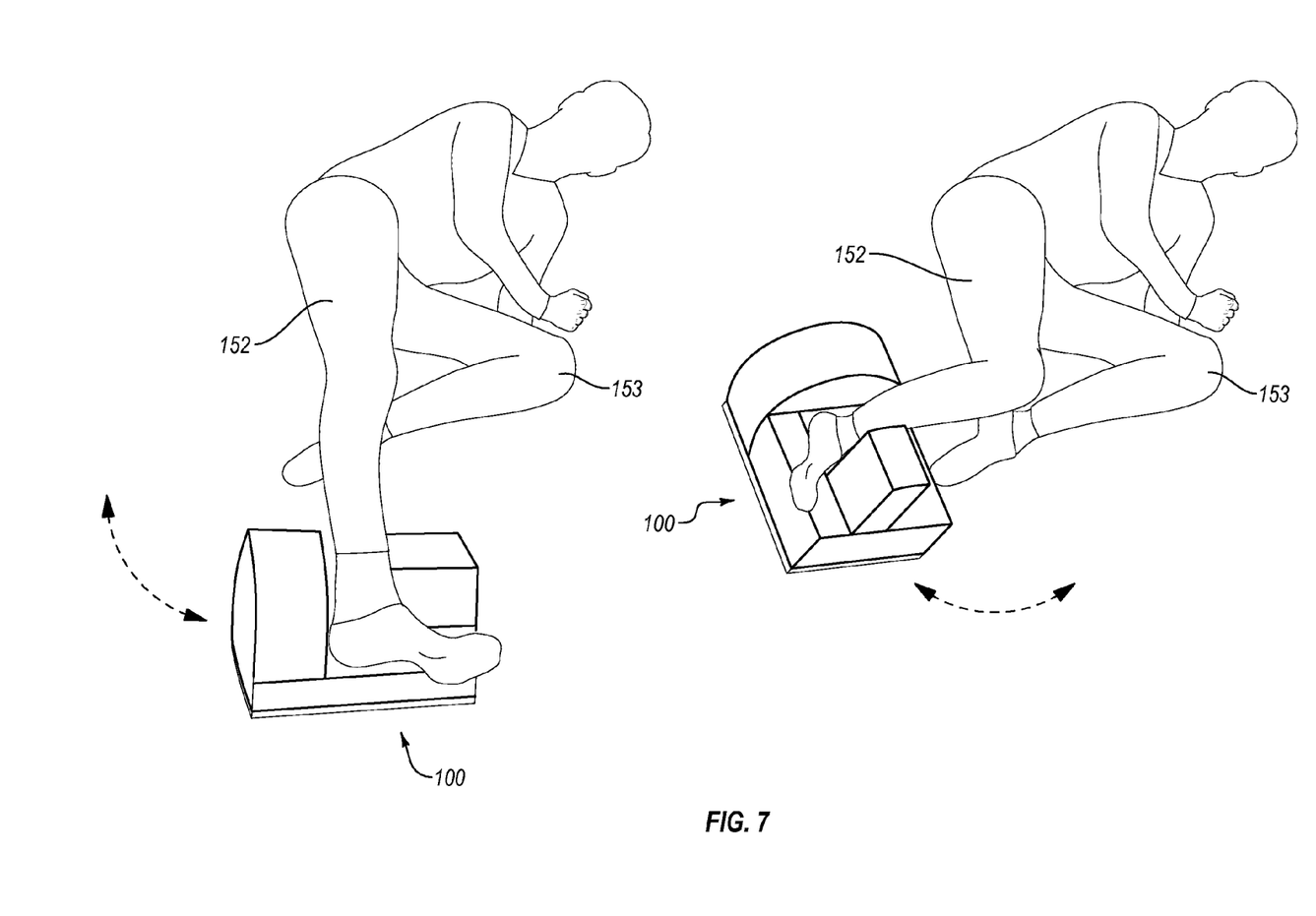
FIG. 7 depicts a user using the orthopedic support and exercise device for knee flexion, extension.

In FIG. 7, a user lies on a side and performs knee flexion and extension movements with a lower limb and the device while the other limb remains in a neutral position. Here, the right leg 152 performs knee flexion and extension while the left leg 153 remains neutral. Turning the orthopedic support and exercise device 100 around 180 degrees, the left leg 153 may perform knee flexion and extension while the right leg 152 remains neutral.

Embodiments anticipate further exercises be performed with the orthopedic support and exercise device 100. Embodiments include isolation such that no movement is performed. Embodiments further include exercises where both lower limbs have movement.

Figure 8:
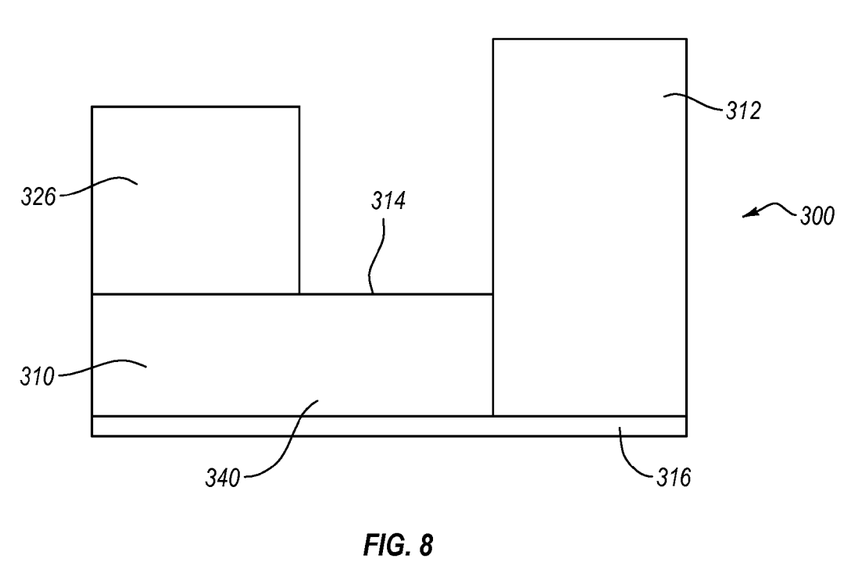
FIG. 8 depicts an orthopedic support and exercise device with the foot support body, the rotation restraint wall, and the divider wall formed by attachment.

Although the orthopedic support and exercise device 100 may include that the foot support body, the rotation restraint wall, and the divider wall be formed from one body such that no attachment is required, alternatives include that elements be attached. Turning to FIG. 8, an orthopedic support and exercise device 300 is shown with separate elements of a foot support body 310, a rotation restraint wall 312, a divider wall 326 formed by attachment, an ankle bed rest 314 between the rotation restraint wall 312 and divider wall 326, and a weighted slider 316 beneath the foot support body 310 and the rotation restraint wall 312. The rotation restraint wall 312 and the divider wall 326 may be attached to the foot support body 310 by an adhesive or other secure means commonly known in the art. Alternatively, a skin layer 340 may be used to secure the rotation restraint wall 312 and the divider wall 326 to the foot support body 310.

One or more of the foot support body, rotation restraint wall, and the divider wall may be made of lightweight polymer foam, open cell polyurethane, foams, plastics, composites, metal, rubber, and other types of material.

The present disclosure may be embodied in other specific forms without departing from its spirit or characteristics. The described embodiments are to be considered as illustrative and not restrictive. The scope of the disclosure is, therefore, indicated by the appended claims rather than by the foregoing description. Changes that come within the meaning and range of equivalency of the claims are to be embraced within their scope.

What is claimed is:

1. An orthopedic support and exercise device comprising:
   a foot support body;
   a rotation restraint wall extending vertically upward from the foot support body and located along one side of the foot support body;
   a divider wall extending vertically upward from the support body and extending transversely from an opposing side of the foot support body,
   an ankle bed rest with a surface defined by a space between an inner surface of the rotation restraint wall and an inner surface of the divider wall such that a foot placed on the orthopedic support and exercise device with an ankle of the foot in the ankle bed rest is prevented from rotational movements during extension and flexion of a leg; and
   a weighted slider with a smooth bottom surface that is attached in a flush manner to a base of the foot support body such that an entire surface of the weighted slider rests flat against the base of the foot support body.

2. The orthopedic support and exercise device in claim 1, further comprising a recess in the foot support body located in the ankle bed rest.

3. The orthopedic support and exercise device in claim 2, wherein the recess extends horizontally between the divider wall and the rotation restraint wall.

4. The orthopedic support and exercise device in claim 2, wherein the recess extends vertically at least a length equal to a width of the divider wall.

5. The orthopedic support and exercise device in claim 1, further comprising a skin layer that includes a polymer coating around an outer surface of the orthopedic support and exercise device.

6. The orthopedic support and exercise device in claim 1, further comprising a skin layer that includes a polymer coating around the one or more of the foot support body, the rotation restraint wall, the divider wall, and the slider.

7. The orthopedic support and exercise device in claim 1, further comprising a skin layer around an outer surface of the orthopedic support and exercise device that makes the orthopedic support and exercise device reusable.

8. The orthopedic support and exercise device in claim 1, wherein the divider wall separates a top space for a right foot support and a bottom space for a left foot support.

9. The orthopedic support and exercise device in claim 1, wherein the foot support body prevents rotational movement of one or more of dorsiflexion, plantarflexion, inversion, eversion, and circumlocution.

10. The orthopedic support and exercise device in claim 1, wherein the weighted slider comprises polished wood or a polished laminate.

11. The orthopedic support and exercise device in claim 1, wherein the foot support body, rotation restraint wall, and the divider wall are made of lightweight polymer foam.

12. The orthopedic support and exercise device in claim 1, wherein the foot support body, the rotation restraint wall, and the divider wall comprises open cell polyurethane material.

13. The orthopedic support and exercise device in claim 1, wherein the rotation restraint wall and the divider wall are attached to the foot support body by an adhesive.

14. The orthopedic support and exercise device in claim 1, wherein the foot support body, the rotation restraint wall, and the divider wall are formed from one body such that no attachment is required.

15. A method for supporting and restraining a patient's ankle while performing leg exercises, the method comprising:
   with a patient lying on a side, positioning an orthopedic support and exercise device under an ankle region of the patient;
   placing the patient's ankle on an ankle bed rest of the device, thereby supporting the patient's ankle;
   the patient performing with one leg and one foot one or more of hip flexion, hip extension, knee flexion, and knee extension with the patient's foot inserted into the orthopedic support and exercise device and the patient's foot in a side position; and
   maintaining another leg of the patient in a neutral position.

16. The method in claim 15, further comprising:

lying in a supine position;

performing with one leg and one foot of the patient one or more of hip abduction, hip adduction, knee plus hip flexion, and knee plus hip extension, with the patient's foot inserted into the orthopedic support and exercise device and the patient's foot pointing generally upward; and maintaining another leg of the patient in a neutral position.

17. An orthopedic support and exercise device comprising:

a foot support body;

a rotation restraint wall extending vertically upward from the foot support body and located along one side of the foot support body;

a divider wall extending vertically upward from the support body and extending transversely from an opposing side of the foot support body, an ankle bed rest with a surface defined by a space between an inner surface of the rotation restraint wall and an inner surface of the divider wall such that a foot placed on the orthopedic support and exercise device with an ankle of the foot in the ankle bed rest is prevented from rotational movements during extension and flexion of a leg; and a weighted slider with a smooth bottom surface that is attached to a base of the foot support body, wherein the foot support body, rotation restraint wall, and the divider wall are made of lightweight polymer foam.

18. An orthopedic support and exercise device comprising:

a foot support body;

a rotation restraint wall extending vertically upward from the foot support body and located along one side of the foot support body;

a divider wall extending vertically upward from the support body and extending transversely from an opposing side of the foot support body, an ankle bed rest with a surface defined by a space between an inner surface of the rotation restraint wall and an inner surface of the divider wall such that a foot placed on the orthopedic support and exercise device with an ankle of the foot in the ankle bed rest is prevented from rotational movements during extension and flexion of a leg; and a weighted slider with a smooth bottom surface that is attached to a base of the foot support body, wherein the foot support body, the rotation restraint wall, and the divider wall comprises open cell polyurethane material.

19. An orthopedic support and exercise device comprising:

a foot support body;

a rotation restraint wall extending vertically upward from the foot support body and located along one side of the foot support body;

a divider wall extending vertically upward from the support body and extending transversely from an opposing side of the foot support body, an ankle bed rest with a surface defined by a space between an inner surface of the rotation restraint wall and an inner surface of the divider wall such that a foot placed on the orthopedic support and exercise device with an ankle of the foot in the ankle bed rest is prevented from rotational movements during extension and flexion of a leg; and a weighted slider with a smooth bottom surface that is attached to a base of the foot support body, wherein the weighted slider comprises polished wood or a polished laminate.

\* \* \* \* \*